United States Patent [19]

Yamamoto et al.

[11] Patent Number: 5,182,206

[45] Date of Patent: Jan. 26, 1993

[54] PYRIMINE-PRODUCING BACTERIA

[75] Inventors: Masanori Yamamoto, Kaizuka; Toshio Nakayama, Nara; Osamu Fujii, Nishinomiya; Rie Okabe, Osaka, all of Japan

[73] Assignee: House Food Industrial Co., Ltd., Higashi-Osaka, Japan

[21] Appl. No.: 804,586

[22] Filed: Dec. 10, 1991

Related U.S. Application Data

[62] Division of Ser. No. 544,258, Jun. 26, 1990, Pat. No. 5,108,924.

[30] Foreign Application Priority Data

| Jun. 27, 1989 | [JP] | Japan | 1-164774 |
| Jun. 27, 1989 | [JP] | Japan | 1-164775 |
| Jun. 27, 1989 | [JP] | Japan | 1-164776 |
| Jun. 27, 1989 | [JP] | Japan | 1-164777 |

[51] Int. Cl.$^5$ .................. C12P 13/00; C12P 13/04; C12P 17/10; C12R 1/38
[52] U.S. Cl. ................... 435/253.3; 435/106; 435/117; 435/121; 435/874; 435/875; 435/876; 435/877
[58] Field of Search ............ 435/253.3, 106, 117, 435/121, 253.34, 874, 875, 876, 877

[56] References Cited

U.S. PATENT DOCUMENTS 4,780,238 10/1988 Premuzic ............................ 252/184

OTHER PUBLICATIONS

Shiman et al "Biochem" 1965 4 No. 10 pp. 2233-2236.
JPOABS Sugisawa et al (J62331111) Oct. 1989.

*Primary Examiner*—Herbert J. Lilling
*Attorney, Agent, or Firm*—Oblon, Spivak, McClelland, Maier & Neustadt

[57] ABSTRACT

A novel pyrimine-producing strain belonging to genus Pseudomonas exhibits the following bacteriological properties: denitrification reaction: negative; assimilation of carbon sources:
D-arabinose: positive
L-lysine: negative and a novel pyrimine-producing strain belonging to genus Pseudomonas exhibits the following bacteriological properties: denitrification reaction: negative, assimilation of carbon sources:
D-arabinose: positive
L-lysine: positive These novel strains produce pyrimine in high yield and if the strains are cultured in a proper culture medium in the presence of an iron salt, a natural red dye, ferropyrimine, can be easily produced and directly be recovered from the culture medium.

2 Claims, No Drawings

PYRIMINE-PRODUCING BACTERIA

This is a division of application Ser. No. 07/544,258, filed on Jun. 26, 1990, now U.S. Pat. No. 5,108,924.

BACKGROUND OF THE INVENTION

The present invention relates to bacteria which can produce pyrimine useful as an intermediate of a natural dye, ferropyrimine, and to a method for effectively preparing pyrimine in which the pyrimine-producing bacteria are used.

Natural dyes have recently attracted much attention since doubt has arisen regarding the safety of synthetic dyes. Among such natural dyes, a natural red dye, ferropyrimine, has been produced by culturing a GH-strain belonging to genus Pseudomonas in a culture medium to have the strain produce pyrimine and simultaneously associate the resulting pyrimine with iron ions which are added to the culture medium in advance and isolating the thus formed ferropyrimine from the culture medium (see Biochemistry, 1965, 4, No. 10).

SUMMARY OF THE INVENTION

An object of the present invention is to provide novel pyrimine-producing bacteria.

Another object of the present invention is to provide a method for effectively preparing pyrimine.

These and other objects of the present invention will be apparent from the following description and Examples.

According to one aspect of the present invention there is provided a first and novel pyrimine-producing strain belonging to genus Pseudomonas exhibiting the following bacteriological properties:
Denitrification reaction: negative
Assimilation of carbon sources:
 D-arabinose: positive
 L-lysine: negative According to another aspect of the present invention, there is provided a second and novel pyrimine-producing strain belonging to genus Pseudomonas exhibiting the following bacteriological properties:
Denitrification reaction: negative
Assimilation of carbon sources:
 D-arabinose: positive
 L-lysine: positive These strains produce pyrimine in an amount of not less than 400 μg/ml when they are cultured in the presence of a plant in an LS basal medium and they start production of pyrimine at latest 8 days after the initiation of the cultivation.

According to a further aspect of the present invention, there is provided a method for preparing pyrimine which comprises the steps of subjecting a pyrimine-producing strain to a mixed cultivation in a culture medium in the presence of a plant and isolating pyrimine produced from the culture medium.

According to another aspect of the present invention, there is provided a method for preparing pyrimine which comprises the steps of culturing pyrimine-producing bacteria belonging to genus Pseudomonas, in the presence of a plant, in a culture medium containing sugar, a nitrogen atom-containing compound, a magnesium atom-containing compound, a phosphorus atom-containing compound and iron atom-containing compound, but free of calcium and chloride ions and then isolating the resulting pyrimine.

According to another aspect of the present invention, there is provided a method for preparing pyrimine which comprises the steps of culturing pyrimine-producing bacteria belonging to genus Pseudomonas in a culture medium containing an organic nitrogen atom-containing compound, sugar, an inorganic nitrogen atom-containing compound, a phosphorus atom-containing compound and iron atom-containing compound, but free of calcium and chloride ions, and having a pH ranging from 3.8 to 5, and then isolating the resulting pyrimine.

DESCRIPTION OF THE PREFERRED EMBODIMENTS

The first and novel pyrimine-producing strain of the present invention has the following bacteriological properties:

Bacteriological Properties

1. Morphological Properties
   Morphology: bacillus which exists independently or is attached in the form of a chain and does not form a spore;
   Motility: It has motility and a polar flagellum;
   Size: 0.6~0.8μ × 1.0~3.5μ;
   Gram-staining: negative;
2. Cultivability in Various Culture Mediums
   (1) Bouillon Culture
       Growth: moderate; Tunic: It forms a ring;
       Precipitates: slightly present; Turbidity: observed.
   (2) Bouillon Slant Culture
       Shape: fibrous; Surface: smooth and glossy;
       Periphery: It forms entire colonies;
       Color Tone: milk-white;
       Transparency: opaque.
   (3) Bouillon Agar Plate Culture
       Shape: perfect circle;
       Periphery: It forms entire colonies;
       Shape of Surface Protuberance: lens-like shape;
       Surface: smooth and glossy; Color Tone: milk-white;
   (4) Bouillon Agar Stab Culture
       It grows on the surface of the culture medium and along the upper portion of the stab.
3. Physiological Properties
   (1) Behavior Against Oxygen: aerobic;
   (2) Catalase: +
   (3) Oxidase: +
   (4) Arginine Dehydrolase: —
   (5) Lipase: + (hydrolyzation of Tween 80)
   (6) Lecithinase: — (decomposition of yolk)
   (7) Hydrolyzation of Gelatin: —
   (8) Hydrolyzation of Starch: —
   (9) Hydrolyzation of Extracellular Poly-β-hydroxybutyric acid (PHB): —
   (10) Autotrophic Growth with use of $H_2$: —
   (11) Formation of Dye:
       It does not form any dye in Pseudomonas F agar and Pseudomonas P agar.
   (12) Reduction of Nitrates: —
   (13) Denitrification Reaction: —
   (14) Decomposition point in protocatechulate: ortho-position
   (15) Intracellular Accumulation of PHB: +
   (16) Formation of Levan from Sucrose: —
   (17) Growth Temperature Range: from 11 to 40° C.; optimum growth temperature: 30 to 32° C.
   (18) Growth pH Range: from 3.8 to 8.5; optimum growth pH: 5.5 to 6.5.
   (19) Assimilation of Carbon Sources:

| | | | |
|---|---|---|---|
| D-glucose: | + | D-fructose: | + |
| D-arabinose: | + | trehalose: | ± |
| mannitol: | + | inositol: | + |
| glycerol: | + | L-lysine: | — |
| L-valine: | ± | β-alanine: | + |

| Bacteriological Properties | |
|---|---|
| glycolate: + | p-hydroxybenzoate: + |

The classification of the strain of the present invention was carried out according to the method disclosed in "Bergey's Manual of Systematic Bacteriology", 1984, Vol. 1 on the basis of the foregoing bacteriological properties. As a result, this strain is a gram-negative bacillus which shows motility by a polar flagellum, is aerobic, is positive to catalase test and is positive to oxidase test. Therefore, this strain was judged to be a bacillus belonging to genus Pseudomonas.

Among strains belonging to genus Pseudomonas, *Pseudomonas cepacia* and *Pseudomonas gladioli* are known as strains which intracellularly accumulate poly-β-hydroxybutyric acid as a carbon source-storage substance, grow at 40° C. and decomposes protacatechuic acid at the ortho-position.

However, this strain cannot use sucrose, but can use glycine as a carbon source, as will be shown below. The strain (*Pseudomonas cepacia*) differs from the strain of this invention (Pseudomonas sp. K-2) in these points.

| Properties | Pseudomonas sp. K-2 | Pseudomonas cepacia |
|---|---|---|
| Assimilation of Hydrocarbon Sucrose | − | + |
| Glycine | + | − |

On the other hand, this strain cannot form levan from sucrose, cannot hydrolyze gelatin and has no lecithinase as will be shown below. The strain (*Pseudomonas gladioli*) differs from the strain of this invention (Pseudomonas sp. K-2) in these points.

| Properties | Pseudomonas sp. K-2 | Pseudomonas gladioli |
|---|---|---|
| Formation of levan from sucrose | − | + |
| Hydrolyzation of glatin | − | + |
| Lecithimase | − | + |

Therefore, it is reasonable to judge that the present strain is a novel strain belonging to genus Pseudomonas and was named Pseudomonas sp. K-2. The present strain is deposited with the Fermentation Research Institute (FRI) under the accession No. FERM BP-2933.

The second pyrimine-producing strain according to the present invention has the same bacteriological properties as those of the first pyrimine-producing strain of the present invention except for the following points:
Growth Temperature Range: 11° to 35° C.
Assimilation of Carbon Sources: L-lysine +

Therefore, this strain was judged to be a bacillus belonging to genus Pseudomonas.

Among strains belonging to genus Pseudomonas, *Pseudomonas solanacearum* is known as strains which intracellularly accumulates poly- β-hydroxybutyric acid as a carbon source-storage substance, does not grow at 40° C. and decomposes protocatechuic acid at the ortho-position.

However, this strain (*Pseudomonas solanacearum*) can under undergo a denitrification reaction and cannot use D-arabinose as a carbon source, as will be shown below.

The strain (*Pseudomonas solanacearum*) differs from the strain of this invention (*Pseudomonas sp.* K-1) in these points.

| Properties | Pseudomonas sp. K-1 | Pseudomonas solanacearum |
|---|---|---|
| Denitrification Reaction | − | + |
| Assimilation of Hydrocarbon D-arabinose | + | − |

Therefore, it is reasonable to judge that the present strain is a novel strain belonging to genus Pseudomonas and was named Pseudomonas sp. K-1. The present strain is deposited with the Fermentation Research Institute (FRI) under the accession No. FREM BP-2932.

When the foregoing strains, Pseudomonas sp. K-2 and Pseudomonas sp. K-1, are cultured, it is preferred that they are first subjected to a pre-cultivation at a temperature of about 25° C. for 2 to 3 days in a culture medium such as a nutrient agar culture medium or an improved GS culture medium and then directly inoculated into an LS culture medium, but it is also possible to directly inoculate and culture the strains in an LS culture medium.

If the foregoing strains sp. K-2 and sp. K-1 or other pyrimine-producing strains are cultured in the presence of a plant, pyrimine can be obtained in high efficiency. As such plants, there may be suitably used, for instance, plants of the Liliaceae family such as Welsh onion; plants of the Cruciferae family such as lettuce, cabbage, Japanese dale horseradish, Japanese radish and water cress; plants of the Perilla family such as perilla, basil and mint; plants of the Polygonaceae family such as *Rumex acetosa;* plants of the Leguminosae family such as haricot bean; plants of the Solanaceae family such as tomato, eggplant and guinea pepper; and plants of the Gesneriaceae family such as centoporia.

Sections of mesophyll, stem, rhizome or the like of these plants are inoculated into an LS agar culture medium to which a hormone such as β-naphthylacetic acid or kinetin is supplemented under sterilized conditions and then the differentiation thereof is induced and the resulting product is preferably employed in the present invention as such a plant. Alternatively, it is also preferable to use those obtained by sowing seeds of such a plant which have been subjected to sterilization treatment in the same LS agar culture medium to thus have them germinate and grow.

Moreover, it is further possible to use plant cells (such as cells of tobacco) and callus obtained by sterilizing a plant body, and inoculating the resulting pieces of explant into a culture medium under sterile conditions to induce callus formation. The amount of the plants to be added to the culture medium is not critical, but it in general ranges from 0.01 to 5 g and preferably 0.1 to 0.5 g per 100 parts by weight of the culture medium. In addition, the density of the strain to be inoculated into the culture medium desirably ranges of not less than $10^5$/ml, more desirably about $10^5$ to $10^7$/ml.

The culture medium used for subjecting the foregoing strains and the plants to a mixed cultivation comprises the following components which are commonly incorporated into culture mediums:
(i) Carbon Sources: sugars such as glucose, fructose, sucrose and/or sugar alcohols such as glycerol;

(ii) Nitrogen Sources: inorganic nitrogen atom-containing compounds such as ammonium salts and/or nitrates;
(iii) Inorganic Salts: phosphates, sulfates or the like of metals such as potassium and magnesium.

In the present invention, it is advantageous that ferric ions are added to the culture medium in advance in order to directly obtain ferropyrimine from pyrimine produced by the strain during the cultivation thereof. Such iron ions can be supplied to the culture medium in the form of salts such as ferric sulfate. The amount of the ferric ions in the culture medium is desirably not less than 10 ppm and preferably 20 to 100 ppm expressed in the amount of salts.

The culture mediums used for producing pyrimine may be either solid or liquid. Moreover, the strains of the present invention can be cultured by a variety of methods, but preferably they are cultured by a rotary shaking culture or an aeration-agitation culture. In addition, the strains are preferably cultured under aerobic conditions. For instance, they can be cultured while being irradiated with light rays. The culture conditions are properly selected and adjusted so that the maximum amount of the intended pyrimine can be accumulated in the culture medium. Preferred culture conditions are as follows:
(i) pH of Initial Culture Medium: 3.8 to 7.0; more preferably 5.0 to 6.0.
(ii) Cultivation Temperature Range: 15° to 30° C.; more preferably 20° to 25° C.
(iii) (Cultivation Time: 8 to 20 days.
(iv) pH of Culture Medium during the culturing: 3.8 to 6.0, preferably 4.0 to 4.5.

Any known means can be adopted for isolating and purifying the pyrimine produced by the strain and accumulated in the culture medium according to the foregoing method.

The foregoing pyrimine-producing strains of the present invention and other pyrimine-producing strains are subjected to a mixed culture in the presence of a plant in one of culture mediums explained above. However, the optimum yield of pyrimine can be achieved by use of a culture medium which comprises a sugar, a nitrogen atom-containing compound, a magnesium atom-containing compound, a phosphorus atom-containing compound and an iron atom-containing compound, but is free of calcium and chloride ions. More specifically, the culture medium used in the present invention comprises, for instance, 20 to 80 g, preferably 30 to 60 g of sugar; 1.0 to 5.0 g, preferably 1.5 to 3.5 g of a nitrogen atom-containing compound; 0.1 to 0.5 g, preferably 0.3 to 0.45 g of a magnesium atom-containing compound; 0.1 to 0.8 g, preferably 0.15 to 0.5 g of a phosphorus atom-containing compound; 0.01 to 0.2 g, preferably 0.02 to 0.15 g of an iron atom-containing compound; and the balance of water. The culture medium may further comprise other components free of calcium and/or chloride ion-containing compounds. For instance, it may comprise 0 to 0.2 g of an alkali metal salt of EDTA, 0 to 20 g of agar or the like.

Alternatively, pyrimine can also be obtained, in high yield, by culturing the pyrimine-producing strains, in the presence or absence of a plant, in a culture medium which comprises at least one organic nitrogen atom-containing compound, for example, selected from the group consisting of meat extract, proteose peptone, casamino acids, powdery soy protein products and corn steep liquor; a sugar, an inorganic nitrogen atom-containing compound, a phosphorus atom-containing compound and an iron atom-containing compound, but is free of calcium and chloride ions. Examples of the inorganic nitrogen atom-containing compounds are ammonium salts and nitrates. The phosphorus atom-containing compound supplies phosphate ions to the culture medium and typical examples thereof are potassium phosphate and sodium phosphate. The iron atom-containing compound supplies iron ions to the culture medium and typical examples thereof include ferric sulfate. As has been explained above, if ferric ions are present in the culture medium in advance, ferropyrimine can directly be recovered from the culture medium.

A specific example of such a culture medium comprises, per liter thereof, 20 to 80 g, preferably 25 to 75 g of a sugar; 1 to 5 g, preferably 1.5 to 3.5 g of an inorganic nitrogen atom-containing compound; 0.2 to 1 g, preferably 0.25 to 0.6 g of a phosphorus atom-containing compound; 0.01 to 0.2 g, preferably 0.02 to 0.15 g of an iron atom-containing compound; 0.1 to 4 g, preferably 0.2 to 2 g of an organic nitrogen atom-containing compound; and the balance of water. The culture medium of this kind may further comprise other components which are free of calcium and chloride ions. For instance, it may comprise 0 to 0.45 g of a magnesium atom-containing compound such as magnesium sulfate; 0 to 0.2 g of an alkali metal salt of EDTA; 0 to 20 g of agar and so forth. In this connection, 1M potassium phosphate buffer (pH 5) is employed as the phosphorus atom-containing compound and, in this case, the buffer is used in an amount ranging from 100 to 200 g.

According to the present invention, there are provided novel strains belonging to genus Pseudomonas which can produce pyrimine in high yield as well as a novel method for preparing pyrimine with the use of such strains. Moreover, if the strains are cultured in a proper culture medium in the presence of iron salts, a natural red dye, i.e., ferropyrimine, can be easily and directly obtained from the culture medium.

The present invention will hereinafter be described in more detail with reference to the following non-limitative working Examples.

EXAMPLE 1

0.1 mg/l each of α-naphthylacetic acid and kinetin was added to a Linsmaier-Skoog basal medium (1650 mg of $NH_4NO_3$; 1900 mg of $KNO_3$; 440 mg of $CaCl_2.2H_2O$; 370 mg of $MgSO_4.7H_2O$; 170 mg of $KH_2PO_4$; 6.2 mg of $H_3BO_3$; 22.3 mg of $MnSO_4.4H_2O$; 8.6 mg of $ZnSO_4.7H_2O$; 0.83 mg of KI; 0.25 mg of $Na_2MoO_4.2H_2O$; 0.025 mg of $CoCl_2.6H_2O$; 0.025 mg of $CuSO_4.5H_2O$; 37.3 mg of $Na_2$-EDTA; 27.8 mg of $FeSO_4.7H_2O$; 100 mg of myoinositol; 0.4 mg of thiamin hydrochloride; 30,000 mg of sucrose; 1,000 ml of distilled water) and then the pH of the resulting solution was adjusted to 5.8 to obtain a culture medium (hereunder referred to as "LS culture medium"). The LS culture medium was dispensed as 50 ml portions into ten 300 ml volume Erlenmeyer flasks and the flasks were sealed with adsorbent wadding plugs to perform sterilization at 121° C. for 15 minutes. After cooling, there was inoculated, into the sterilized LS culture medium, seedlings of horseradish which had been separately grown in an LS agar culture medium (0.8% of agar) under sterile conditions and a loopful of the strain, Pseudomonas sp. K-2, which had been separately grown in an improved GS culture medium (the preparation thereof will be detailed below). The culture was performed at 25° C. in accordance with a rotary shaking culture (150 rpm) under irradiation with light rays.

After 17 days, the culture medium was centrifuged to remove the cell bodies or the like and the resulting supernatant was filtered through a membrane filter having a pore size of 0.45 μm. After the addition of an $FeSO_4.7H_2O$ solution (278 mg/l) to the filtrate, the absorbance thereof was determined at 558 nm to estimate the amount of pyrimine present in the culture medium in terms of a calibration curve and it was found to be 1650 μg/ml. The production of pyrimine was started on the sixth day of cultivation.

Improved GS Culture Medium (i) A solution (a) was prepared so that it had the following composition: 30,000 mg of glucose; 770 mg of meat extract (available from Difco Laboratories); 1650 mg of $NH_4NO_3$; 370 mg of $MgSO_4.7H_2O$; 27.8 mg of $FeSO_4.7H_2O$; 37.3 mg of $Na_2$-EDTA; 20,000 mg of agar; and 1,000 ml of distilled water. The pH value thereof was controlled to 6.0 by the addition of 1N KOH.

(ii) A solution (b): 1M potassium phosphate buffer (pH 6.0).

The improved GS culture medium was prepared by treating the solutions (a) and (b) in an autoclave at 121° C. for 15 minutes to perform sterilization and mixing the autoclaved solutions (a) and (b) in a ratio of 2 ml of the solution (b) per 11 ml of the solution (a).

EXAMPLE 2

The same procedures used in Example 1 were repeated except that the strain, Pseudomonas sp. K-1 was substituted for the strain Pseudomonas sp. K-2 used in Example 1. After 17 days, the content of ferropyrimine in the resulting culture medium was determined in terms of a calibration curve and it was found to be 1750 μg/ml. The production of pyrimine was started on the fifth day of cultivation.

EXAMPLE 3

An improved S culture medium which comprised 30,000 mg of sucrose; 1650 mg of $NH_4NO_3$; 370 mg of $MgSO_4.7H_2O$; 500 mg of $KH_2PO_4$; 27.8 mg of $FeSO_4.7H_2O$; 37.3 mg of $Na_2$-EDTA; and 1,000 ml of distilled water and had a pH of 7.0 was dispensed as 50 ml portions into two 300 ml volume Erlenmeyer flasks and the flasks were sealed with adsorbent wadding plugs to perform sterilization at 121° C. for 15 minutes. After cooling, there were inoculated, into the sterilized LS culture medium, seedlings of horseradish which had been separately grown in a LS agar culture medium (0.8% of agar) under sterile conditions and a loopful of the strain, Pseudomonas sp. K-1, which had been separately grown in an improved GS culture medium (the preparation thereof will be detailed below). The culture was performed at 25° C. in accordance with a rotary shaking culture (150 rpm) while irradiating with light rays.

After 12 days, the culture medium was centrifuged to remove the cell bodies or the like, and the resulting supernatant was filtered through a membrane filter having a pore size of 0.45 μm. After the addition of an $FeSO_47H_2O$ solution (278 mg/l) to the filtrate, the absorbance thereof was determined at 558 nm to evaluate the amount of ferropyrimine present in the culture medium in terms of a calibration curve and it was found to be 1360 μg/ml.

EXAMPLE 4

The same procedure used in Example 3 were repeated except that the strain, Pseudomonas sp. K-2 was substituted for the strain Pseudomonas sp. K-1 used in Example 3 and that after 13 days, the culture medium was centrifuged to remove the cell bodies and the like. The content of ferropyrimine in the resulting culture medium was found to be 940 μg/ml.

EXAMPLE 5

The following solutions were prepared:
(a) a solution of 36,000 mg of glucose in 300 ml of distilled water;
(b) a solution obtained by dissolving 1980 mg of $NH_4NO_3$, 220 mg of $MgSO_4.7H_2O$, 300 mg of $KH_2PO_4$, 16.68 mg of $FeSO_4.7H_2O$ and 22.38 mg of $Na_2$-EDTA in 300 ml of distilled water and then adjusting the pH thereof to 6.0 with 1N KOH;
(c) a solution of 1,200 mg of meat extract (available from Difco Laboratories) in 120 ml of distilled water; and
(d) 120 ml of 1M potassium phosphate buffer (pH 5.0).

The foregoing solutions (a) to (d) were sterilized at 121° C. for 15 minutes and introduced into a 2 l volume jar fermenter (sterilized) to mix them under sterile conditions. Separately, the strain, Pseudomonas sp. K-2 was pre-cultured at 25° C. for 48 hours by a shaking culture technique in a 300 ml volume Erlenmeyer flask containing a culture medium which was prepared in the same manner and had the same composition as above. 84 ml of the precultured strain was inoculated into the culture medium contained in the jar fermenter and cultured at 25° C. by an aeration-agitation culture (flow rate of air=1.5 l/min; rate of revolution=300 to 400 rpm).

After the second day of cultivation, the culture was performed while adjusting the pH value of the culture medium to 4.2 to 4.5 by the addition of 1N KOH and 1N phosphoric acid.

After 12 days, the culture medium was centrifuged to remove the cell bodies and the like, and the resulting supernatant was filtered through a membrane filter having a pore size of 0.45 μm. After the addition of an $FeSO_4.7H_2O$ solution (278 mg/l) to the filtrate, the absorbance thereof was determined at 558 nm to evaluate the amount of ferropyrimine present in the culture medium in terms of a calibration curve and it was found to be 1940 μg/ml.

EXAMPLE 6

The same procedures used in Example 5 were repeated except that the strain, Pseudomonas sp. K-1 was substituted for the strain Pseudomonas sp. K-2 used in Example 5 and that after 8 days, the culture medium was centrifuged to remove the cell bodies or the like. The content of ferropyrimine in the resulting culture medium was found to be 1950 μg/ml.

What is claimed is:

1. A bacteriologically pure culture of a pyrimine-producing strain belonging to genus Pseudomonas exhibiting the following bacteriological properties:
Dentrification reaction: negative
Assimilation of carbon sources:
   D-arabinose: positive
   L-lysine: negative
wherein it produces pyrimine in an amount of not less then 400 μg/ml when it is cultured in the presence of a plant in an LS basal medium and it starts production of pyrimine at latest 8 days after the initiation of the culture.

2. The strain of claim 1 wherein it is a strain FERM BP-2933.

* * * * *